United States Patent [19]

Alexander et al.

[11] Patent Number: 4,761,237

[45] Date of Patent: Aug. 2, 1988

[54] PERITONEAL DIALYSIS SOLUTION CONTAINING CARBOHYDRATE POLYMERS

[75] Inventors: Steven R. Alexander, Tigard; W. Michael Myers, Tualatin, both of Oreg.

[73] Assignee: Baxter Travenol Laboratories, Inc., Deerfield, Ill.

[21] Appl. No.: 65,656

[22] Filed: Jun. 22, 1987

Related U.S. Application Data

[63] Continuation of Ser. No. 888,263, Jul. 18, 1986, abandoned, which is a continuation of Ser. No. 282,309, Jul. 10, 1981, abandoned.

[51] Int. Cl.$^4$ ............................................. B01D 13/00
[52] U.S. Cl. ..................................... 210/647; 210/927
[58] Field of Search ..................... 210/644, 645, 321.3, 210/927, 646, 647; 128/DIG. 3; 424/180; 604/27-29; 514/60

[56] References Cited

U.S. PATENT DOCUMENTS

| | | | |
|---|---|---|---|
| 3,525,686 | 8/1970 | Roberts | 210/321.2 X |
| 3,911,915 | 10/1975 | Seifter et al. | 210/646 X |
| 3,928,135 | 12/1975 | Milner | 195/31 R |
| 4,021,543 | 5/1977 | McKay | 424/180 |
| 4,182,756 | 1/1980 | Ramsay et al. | 424/180 |
| 4,308,255 | 12/1981 | Raj et al. | 424/180 X |
| 4,339,433 | 7/1982 | Kartinos et al. | 424/180 X |

OTHER PUBLICATIONS

Ahearn, D. J. et al, "Controlled Sodium Removal. . .", Trans. Am. Soc. Art. Int. Organs, vol. 18, 4/17/72, pp. 423-428.

Article by Jon Gjessing entitled "The Use of Dextran as a Dialysing Fluid in Peritoneal Dialysis", *Acta. Med. Scand.*, vol. 185, pp. 237-239 (1969).

Article of J. Jirka et al. entitled "Peritoneal Dialysis by Iso-Oncotic Dextran Solution in Anaesthetized Dogs Intra-Peritoneal Fluid Volume and Protein Concentration in the Irrigation Fluid", *Proc. Eur. Dial. Transplant Assoc.*, vol. 4, pp. 141-145 (1967).

Gjessing, J., "Addition of Aminoacids to Peritoneal-Dialysis Fluid", The Lancet, 10/12/1968, p. 812.

Whistler, Roy, *Starch:Chemistry and Technology*, vol. 1, Academic Press, N.Y., N.Y., 1965, p. 177.

Kirk-Othmer, *Encyclopedia of Chem. Tech.*, second edition, vol. 6, pp. 919-928, dated 7/7/65.

Glucose Syrups and Related Carbohydrates, G. G. Birch et al, Elsevier Pub. Co., Ltd., 1970, pp. 22-25.

*Primary Examiner*—Frank Sever
*Attorney, Agent, or Firm*—Charles R. Mattenson; Paul C. Flattery

[57] ABSTRACT

A peritoneal dialysis solution which comprises a water solution of physiological pH, and having physiological salts and metabolizable carbohydrate polymers in concentrations sufficient to safely effect the removal of solutes and water from a patient by peritoneal dialysis.

4 Claims, No Drawings

PERITONEAL DIALYSIS SOLUTION CONTAINING CARBOHYDRATE POLYMERS

This is a continuation of co-pending application Ser. No. 888,263, filed on July 18, 1986, now abandoned, which is a continuation of U.S. patent application Ser. No. 282,309, filed July 10, 1981, now abandoned.

TECHNICAL FIELD

The medical procedure known as continuous ambulatory peritoneal dialysis (CAPD) is rapidly growing in clinical acceptance as the technique of choice for maintaining many patients who have lost kidney function. Peritoneal dialysis solution is inserted into the peritoneal cavity, whereby diffusion exchange takes place between the solution and the bloodstream across the natural body membranes, to remove by diffusion the waste products which are normally excreted through the kidneys, typically solutes such as sodium and chloride ions and the other materials normally excreted by the body such as urea, creatinine, and water.

The nature and rate of the materials removed from the body by peritoneal dialysis is a function of the solutes present in the peritoneal dialysis solution. Physiological salts are present in the peritoneal dialysis solution such as sodium chloride, calcium chloride, sodium lactate, and sodium acetate, generally at slightly hypotonic concentrations, except for the calcium, so that excess concentrations of such salts in the bloodstream will diffuse into the peritoneal dialysis solution for removal.

BACKGROUND ART

To remove water from the patient, as is generally necessary, other solutes may be added to generate the necessary osmotic pressure. Typically, this solute is a sugar such as glucose, which may normally be present in peritoneal dialysis solutions in a concentration of at least 0.5 percent by weight. When it is desired to increase the ultrafiltration of water from the patient, higher concentrations of sugar are used.

However, as a disadvantage of this system, during the peritoneal dialysis process, as water diffuses into the peritoneal dialysis solution, sugar present in the peritoneal dialysis solution diffuses into the bloodstream to a significant extent. Accordingly, while the system is safe and effective for increasing the ultrafiltration during peritoneal dialysis, it has certain disadvantages. For example, since the sugar diffuses relatively rapidly from the solution in the peritoneal cavity into the bloodstream, there is a considerable and rapid decrease in the osmolarity of the peritoneal dialysis solution. Accordingly, to obtain the desired amount of ultrafiltration, the initial concentration of sugar in the peritoneal dialysis solution must be relatively high to account for the fact that the osmolarity will fall by diffusion of sugar into the bloodstream.

Particularly in certain pediatric cases, children who are on a CAPD regime often lose significant appetite and fail to adequately gain weight. Accordingly it becomes desirable to administer substantial amounts of calories to the child. In accordance with this invention, desired calories can be administered to the pediatric patient while at the same time excessive concentrations of sugar per se are avoided. Such excessive concentrations of sugar could, of course, unduly raise the osmolarity of the solution and would provide undesirable levels of ultrafiltration to the patient. By this invention, the administration of substantial amounts of calories to the patient can be effected by diffusion from the peritoneal dialysis solution, simultaneously with the maintenance of a desired ultrafiltration rate, and also clearance of metabolic waste products such as urea and creatinine through the peritoneal cavity into the dialysis solution. By a proper balance between sugar and other ingredients as described in this invention in a peritoneal dialysis solution, a proper balance of calories, coupled with a proper rate of ultrafiltration can be provided.

In Ramsay et al. U.S. Pat. No. 4,182,756, it is suggested to use high calorie solutions of low molecular weight glucose polymer mixtures in intravenous administration, since such solutions can provide significant increases in calories per liter over monomeric sugar solutions without being hypertonic. Other related prior art is cited in the same patent.

Milner U.S. Pat. No. 3,928,135 also discusses glucose polymers as ingredients for oral ingestion or intravenous administration.

Seifter et al. U.S. Pat. No. 3,911,915 teaches the dialytic introduction of maltose (a disaccharide) intraperitoneally into warm blooded animals. However, maltose shares in the disadvantages of glucose in that the addition of substantial amounts thereof can result in significant and excessive osmolarity so that inadequate amounts of calories may be provided to the pediatric patient by the peritoneal dialysis route, if the osmolarity is proper.

DISCLOSURE OF INVENTION

In accordance with this invention, a peritoneal dialysis solution is provided which comprises a water solution of physiologically tolerable pH, having physiological salts and metabolizable carbohydrate polymers having an average degree of polymerization of at least 4, in concentrations sufficient to safely effect the removal of solutes and water from a patient by peritoneal dialysis.

Basically, the peritoneal dialysis solution of this invention is similar to conventional peritoneal dialysis solutions, which also are of physiologically tolerable pH and have physiological salts such as sodium chloride, calcium chloride and sodium acetate in appropriate concentrations. However, a novel feature of this invention is that the sugar of conventional peritoneal dialysis solution is either partially or completely replaced by metabolizable carbohydrate polymers which preferably have an average degree of polymerization of at least 4; i.e., they typically constitute at least tetrasaccharides, while conventional sugars are either monomers such as glucose or fructose, or dimers such as sucrose or maltose.

As the result of this, the metabolizable carbohydrate polymers exert their osmotic effect to enhance the ultrafiltration of water into the peritoneal dialysis solution, but at the same time they are of higher molecular weight than the sugars conventionally used in prior art peritoneal dialysis solutions, so that their rate of diffusion from the peritoneal dialysis solution through a body membrane into the bloodstream is significantly slower during the peritoneal dialysis procedure. However, that amount of carbohydrate polymer which does transfer to the bloodstream is metabolizable, so that it can be broken down by the body without ill effect.

Accordingly, since the diffusion of the carbohydrate polymer in the dialysis solution into the peritoneal cavity is relatively slower than the diffusion of mono and disaccharides, the decrease in the osmolarity of the dialysis solution during the course of the peritoneal dialysis procedure is slower in the presence of such glucose polymers than in the peritoneal dialysis solutions of the prior art. This, in turn, means that lower initial osmolarities may be utilized in the peritoneal dialysis solutions of this invention, compared with those of the prior art, while still achieving equal ultrafiltration rates over a predetermined period of time in a peritoneal dialysis procedure such as CAPD.

Also, as stated above, large amounts of calories may be provided to the patient by the use of the glucose polymers in accordance with this invention, while at the same time the osmolarity and the ultrafiltration can be controlled in a manner which is relatively independent of the amount of potential calories administered to the patient, so that a peritoneal dialysis solution can be provided which is tailormade to provide optimum calories to the patient while also exhibiting optimum ultrafiltration characteristics. The independent control of both of the above parameters can be accomplished by appropriate adjustment of the concentration of glucose or the like in the solution, coupled with a concentration of glucose polymers in accordance with this invention, with additional control being provided by appropriate selection of the degree of polymerization of the glucose polymers of this invention. In other words, in some circumstances glucose polymers which are tetrasaccharides or pentasaccharides may be used. In other cases, octasaccharides may be used.

Preferably, glucose polymers may be used in accordance with this invention. Such glucose polymers are commercially available, and are described in the patents discussed above. Mixtures of glucose polymers may be prepared by the hydrolysis of starch, and a substantial body of known prior art exists relating to the preparation and processing of glucose polymers.

For example, a glucose polymer may be used having an average degree of polymerization (number of saccharide units per molecule) of about 5, in which at least 99 percent of its molecules have less than 26 glucose units; at least 85 percent of its molecules have less than 11 glucose units; and at least 20 percent of its molecules have less than 4 glucose units. However, if desired, carbohydrate polymers having different ranges of degree of polymerization may also be used. Substantially monodisperse polymers, having a relatively uniform degree of polymerization, may also be used if desired.

Typically, the peritoneal dialysis solution of this invention may comprise a water solution at a pH of 5 to 7.4 containing from 116 to 140.mEq/liter of sodium,0 to 6 mEq/liter of calcium, 100 to 144 mEq/liter of chloride, and from 5 to 200 grams per liter of a metabolizable glucose polymer, preferably having an average degree of polymerization of 4 to 10. It is also desirable for from 30 to 45 mEq/liter of lactate or acetate to be present.

Also, other physiological ions such is magnesium, potassium, and carbonate may be present as desired, along with other additives which may have desirable benefit. For example, 0.5 to 25 grams per liter of amino acid salts or protein hydrolyzates may be added to further enhances the ultrafiltration of water into the peritoneal dialysis solution by their natural osmotic effect, and simultaneously to serve as a source of supplemental nitrogen for protein for the patient as they diffuse into the bloodstream. This can counterbalance the protein which the patient loses as a consequence of the peritoneal dialysis procedure, or may constitute the prime source of protein nutrition for the patient. Added sugars such as glucose, maltose, or dextrose may be present as well for purposes of nutrition, as well as creating an osmotic effect for enhancing ultrafiltration. for example 0.5 to 25 grams per liter.

The use of amino acids in peritoneal dialysis solutions is-taught in the preliminary communication on page 812 of the Oct. 12, 1968 issue of the *Lancet*. However, the peritoneal dialysis solutions disclosed there have no teaching of the use of metabolizable carbohydrate polymers in such solutions.

Other metabolizable carbohydrate polymers which may be utilized in this invention include polysaccharides such as polyglucose, in which the carbonyl linkage has been reduced to an alcohol group. Such a material has the advantage of being more compatible with amino acids or polypeptide protein hydrolyzates upon sterilization, in that the formation of undesirable color bodies by reaction between the carbonyl groups and the amino acids upon heating during the sterilization process can be reduced or eliminated.

It is generally preferable for the pH of the solutions to be slightly on the acid side (5.4 to 6.8) to avoid caramelization of the carbohydrate polymers present during sterilization of the solution. However, the pH can be more alkaline than that with less ill effect during sterilization because of the polymeric nature of the sugar added thereto, which tends to stabilize it during the sterilization cycle.

Peritoneal dialysis solution concentrates may be made for later mixing with water to form the desired peritoneal dialysis solution of any desired concentration. Such concentrates may contain, for example, from 130 to 140 mEq/liter of sodium from 3 to 4 mEq/liter of calcium; from 100 to 144 mEq/liter of chloride; and from 5 to 500 grams/liter of a metabolizable glucose polymer as described above. It is also desirable for from 30 to 40 mEq/liter of bicarbonate precursors such as one or more of lactate, acetate, malate, and/or succinate ions to be present. The bicarbonate precursor acid ions mentioned above, as well as other acid ions of the Krebs cycle may be added to also offer advantages in pH control of the peritoneal dialysis solution of this invention. The sodium or potassium salts of such ions, for example, may be used for this purpose, or the free acids. The above concentrate is preferably mixed with a conventional peritoneal dialysis solution. If mixed with water, higher ion concentrations would be desirable.

It is generally preferable for the osmolarity of the solutions of this invention to be from 272 to 700 milliosmols per liter, preferably 279 to 480 milliosmols per liter.

If amino acids or polypeptides are present in the solution, sulfhydryl-type antioxidants, for example N-acyl cysteine, may also be added to stabilize the amino acids in the peritoneal dialysis solution of this invention.

DESCRIPTION OF SPECIFIC EMBODIMENT

A typical solution which is contemplated for use in peritoneal dialysis is a sterile water solution containing the following: dextrose. $H_2O$—15 grams per liter; sodium—132 mEq/liter; calcium—3.4 mEq/liter; chloride—104 mEq/liter; lactate—37 mEq/liter; glucose polymer having a degree of polymerization of greater than 4 (Polycose,sold by Ross)—120 grams per liter. This solution, when sterile, may be utilized as the peritoneal dialysis solution in a conventional CAPD procedure, utilizing the techniques and equipment developed and sold by the Artificial Organs Division of Baxter Travenol Laboratories, Inc., Deerfield, Illinois, so that good ultrafiltration may take place during the peritoneal dialysis procedure, with reduced diffusion of the glucose polymer into the bloodstream of the patient. Such a solution has an ultrafiltration capability equal to or greater than a commercially available peritoneal dialysis solution containing 4.25 weight percent of dextrose.

The above has been offered for illustrative purposes only, and is not intended to limit the scope of the invention of this application, which is as defined in the claims below.

That which is claimed is:

1. A method of performing peritoneal dialysis comprising the steps of
   (a) introducing into the peritoneal cavity of a patient a solution containing physiological salts in concentrations sufficient to effect the removal of solutes by diffusion from the patient's blood across the peritoneal membrane into the solution, and
   (b) reducing the rate of decrease of osmotic pressure with respect to time sufficient to maintain a desired rate of ultrafiltration, by introducing in the solution nonionic starch hydrolyzate glucose polymers in concentrations sufficient to create an osmotic pressure to effect the removal of water by diffusion from the patient's blood across the peritoneal membrane into the solution, the nonionic hydrolyzate glucose polymers having an average degree of polymerization of at least 4 to sustain the osmotic pressure over time due to the relatively slow removal of the polymers by diffusion from the solution across the peritoneal membrane into the patient's blood, when compared to the removal of glucose polymers having an average degree of polymerization less than 4.

2. A method of performing peritoneal dialysis according to claim 1 and further including in said step (b) the introduction of glucose in combination with the nonionic starch hydrolyzate glucose polymers.

3. A method of performing peritoneal dialysis according to claim 1 or 2 wherein, in said step (b), the concentration of the nonionic starch hydrolyzate glucose polymers is sufficient to create an osmolarity of about 272 to about 700 milliosmols per liter of the solution.

4. A method of performing peritoneal dialysis according to claim 3, wherein, in said step (b), the osmolarity created is about 279 to about 480 milliosmols per liter of the solution.

* * * * *